US00PP09966P

United States Patent [19]

Jack et al.

[11] Patent Number: Plant 9,966

[45] Date of Patent: Jul. 15, 1997

[54] CHAMELAUCIUM (WAXFLOWER) PLANT NAMED BLONDIE

[75] Inventors: Brian Jack; Victoria Syme, both of Coorow, Australia

[73] Assignee: New World Plants USA, Escondido, Calif.

[21] Appl. No.: 603,731

[22] Filed: Feb. 20, 1996

[51] Int. Cl.[6] ..... A01H 5/00

[52] U.S. Cl. ..... Plt./54.1

[58] Field of Search ..... Plt./54.1

*Primary Examiner*—James R. Feyrer

*Attorney, Agent, or Firm*—C. A. Whealy

[57] ABSTRACT

A new and distinct interspecific Chamelaucium hybrid cultivar (known commercially as waxflower) distinguished by its strong and erect flowering stems; upright and semi-open growth habit; dense terminal floral display; red purple flower bud color; light creamy white flower color; and good postharvest longevity.

3 Drawing Sheets

The present invention relates to a new and distinct cultivar of Chamelaucium (Waxflower), botanically known as an interspecific Chamelaucium hybrid, and hereinafter referred to by the cultivar name Blondie.

The new cultivar is a product of a planned and controlled breeding program conducted by the inventors in Coorow, Western Australia, Australia. The new cultivar originated from a deliberate cross by the inventors between two different species of the genus Chamelaucium. An unnamed selection of *Chamelaucium megalpetalum* was used as the female or seed parent and the *Chamelaucium uncinatum* cultivar Purple Pride (not patented) was used as the male or pollen parent. Twenty days after the cross-pollination, the immature seed pod was harvested and the developing embryos were aseptically dissected and transferred onto a nutrient agar-based medium for further development. Mature plants developed from these dissected embryos. The cultivar Blondie was discovered and selected by the inventors as a flowering plant within the progeny of the stated cross in a controlled environment in Coorow, Western Australia, Australia.

Asexual propagation of the new cultivar by cuttings taken at Coorow, Western Australia, Australia, and Escondido, Calif., has shown that the unique features of this new Chamelaucium plant are stabilized and reproduced true to type in successive generations of asexual propagation.

The following traits have been repeatedly observed and are determined to be the unique characteristics of the new Chamelaucium. These characteristics in combination distinguish Blondie as a new and distinct cultivar:

1. Strong and erect flowering stems.
2. Upright and semi-open growth habit.
3. Dense terminal floral display.
4. Red purple flower bud color.
5. Light creamy white flower color.
6. Good postharvest longevity.

The new Chamelaucium differs from its seed parent, the selection of *Chamelaucium megalopetalum*, in the following characteristics:

1. Plants of the new Chamelaucium flower faster than plants of the seed parent.
2. The flower bud color is red purple on plants of the new Chamelaucium whereas the flower bud color on plants of the seed parent is red.
3. The floral tubes of the new Chamelaucium are narrow, prominently fluted, and flared compared to the floral tubes of the seed parent.
4. Plants of the new Chamelaucium have more flowers per stem and appear more dense and full than plants of the seed parent.

5. Plants of the new Chamelaucium have broader flowering stems compared to plants of the seed parent.

The new Chamelaucium differs from its pollen parent, the *Chamelaucium uncinatum* cultivar Purple Pride, in the following characteristics:

1. The flower bud color is red purple on plants of the new Chamelaucium whereas the flower bud color on plants of the pollen parent is dark red.
2. The petal color of the new Chamelaucium when opening is white compared to the purple petal color of Purple Pride. At maturity, the petal color of the new Chamelaucium remains white whereas the petal color of Purple Pride is purple. The floral tube color is also different, as the floral tube of the new Chamelaucium is green and the floral tube of Purple Pride is red brown. The floral tube is more narrow and prominently fluted on plants of the new Chamelaucium compared to plants of Purple Pride.
3. Plants of the new Chamelaucium have more flowers per stem and appear more dense and full than plants of Purple Pride.

The new Chamelaucium can be compared to the Chamelaucium cultivar Revelation, disclosed in U.S. Pat. No. P.P. 8,791. Plants of Blondie differ from plans of Revelation in the following characteristics:

1. Plants of the new Chamelaucium have shorter internodes, smaller leaves, and shorter peduncles than plants of Revelation.
2. The flower bud color is red purple on plants of the new Chamelaucium whereas the flower bud color on plants of Revelation is dark red. The floral tube color at the distal end is green on plants of the new Chamelaucium and the floral tube color at the distal end is purple brown on plants of Revelation.
3. The petal shape of the new Chamelaucium is obovate whereas the petal shape of Revelation is round.
4. The petal color of the new Chamelaucium at maturity is white compared to the light violet petal color of Revelation.
5. Plants of the new Chamelaucium have narrow floral tubes compared to plants of Revelation.

A detailed comparison of the new Chamelaucium, its parents and Revelation plants appears in Chart A at the end of the specification.

The new Chamelaucium plant has not been observed under all possible environmental conditions. The phenotype may vary significantly with variations in environment such as temperature and light level, without, however, any variance in genotype.

The accompanying colored photographs show typical specimens of the vegetative growth and flowers of the new Chamelaucium plant, showing the colors as true as it is reasonably possible to obtain in colored reproductions of this type. The first photograph comprises a side perspective view of typical flowering stems of the new Chamelaucium plant grown in Escondido, Calif. This photograph shows the upright and semi-open growth habit of flowering stems of the new Chamelaucium.

The second and third photographs comprise close-up views of the new Chamelaucium's flowers showing the cultivar's unique petal colors that change with the development of the flower.

In the second photograph, flower buds are red purple; and as the flowers open, the petal color is a light creamy white with a light pink blush.

In the third photograph, flowers shown are mature and petal color is light creamy white.

The following observations, measurements, values, and comparisons describe plants grown in Escondico, Calif. Values representing size of plants, flowers and foliage are averages of plants produced under standard commercial cultural practices. Color references are made to The Royal Horticultural Society Colour Chart except where general terms of ordinary dictionary significance are used.

Classification:

*Botanical.*—An interspecific Chamelaucium hybrid, *Chamelaucium megalopetalum*×*Chamelaucium uncinatum* cultivar Blondie.

*Commercial.*—Hybrid waxflower.

Parentage:

*Female or seed parent.*—Selection of *Chamelaucium megalopetalum* (not patented).

*Male or pollen parent.*—*Chamelaucium uncinatum* cultivar Purple Pride (not patented).

Plant description:

*Form.*—Erect, branched woody shrub.

*Growth habit.*—Vigorous, rigid and upright. Semi-open growth habit.

*Flowering stem length.*—1.8 m.

*Foliage description.*—Numerous leaves on one- and two-year-old wood; opposite arrangement; sessile; and aromatic. Internode length: 10.5 mm. Leaf size: Length: 12.7 mm. Width: 1 mm. Shape: Narrowly lanceolate. Texture: Glabrous. Margin: Entire. Aspect: Flat and thick. Color: Dark green sometimes with red tint.

Flower description:

*Flowering season.*—Flowers develop and open throughout the spring.

*Flower longevity.*—Flower are long-lasting on the plant and after cutting, flowers and calyx persistent.

*Flowering habit.*—Flowers develop on thin first-year stems from upper axils. Numerous flowers arranged in terminal clusters, broad and dense floral display.

*Flower shape.*—Rounded outline, flattened cup-shaped floral tube with obovate, slightly cupped, orbicular petals.

*Flower diameter.*—1.7 cm.

*Flower bud.*—Form: Obovate, covered with thin deciduous bracteoles. Diameter: 7 to 8 mm prior to petal opening. Color: With operculum: Purple red (60A). Without operculum: White (155D). Bud tube: Green (144B).

*Petals.*—Quantity: Five. Shape: Rounded, slightly cupped and orbicular. Diameter: 7 mm. Texture: Waxy. Calyx: Five calyx lobes arranged alternately between petals. Color: When opening: Light creamy white (155C/155D). Developing flowers: Light creamy white (155B) with a slight pink blush at times. Mature flowers: Light creamy white (155B). Flower nectary, immature: Yellow green (146B). Flower nectary, mature: Red purple (59A). Calyx lobe, mature: White. Floral tube: Fluting: Prominent. Outine: Flared. Diameter: Narrow, 4.3 mm. Color: Midpoint: Green. Distal end: Green. Peduncles: Length: 6 to 8 mm. Aspect: Upright and erect. Color: Green. Fragrance: Aromatic when crushed.

*Reproductive organs.*—Stamens: Quantity: Ten fertile stamens with ten infertile stamenoids arranged alternatively between stamens. Staminoidal outline: Narrow, triangular. Stamenoidal collar color, mature: Pale pink to purple. Anthers, mature: Width: 0.7 mm. Color: Brown (200D). Filaments: Length: 2.5 mm. Color: White. Pollen: Color: Green Brown. Texture: Waxy and sticky. Pistils: Quantity: One. Style: Length: 7 mm. Color: Immature: White (155D). Mature: White (155D), Stigma: Color, mature: Yellow (17C). Texture: Bearded and pubescent.

*Fruit.*—Shape: Hemispherical. Form: Three-celled capsule formed by the hardened base of the persistent calyx.

Disease resistance: No resistance or susceptibility to plant pathogens has been observed.

CHART A

| CHARACTERISTIC | BLONDIE | PURPLE PRIDE, pollen parent | *Chamelaucium megapetalum* selection, seed parent | REVELATION |
|---|---|---|---|---|
| FLOWER BUD COLOR, WITH OPERCULUM | Red purple 60A | Dark red 46A | Red 46B | Dark red 46A |
| BUD COLOR, WITHOUT OPERCULUM | White 155D | Pale purple 80A | White 155B | White 155D |
| BUD TUBE COLOR | Green 144B | Green 146A | Light green 145A | Green to violet 144A to 77B |
| PETAL SHAPE, AFTER OPENING | Obovate | Obovate | Obovate | Round |
| PETAL COLOR, WHEN OPENING | White 155C/155D | Purple 78A | White 155B | White 155C |
| PETAL COLOR DEVELOPMENT RATE | Slow | Medium | Slow | Fast |
| PETAL COLOR, MATURE | White 155B | Red purple 59B/59C | White 155D | Light violet 84B |
| FLOWER NECTARY COLOR, IMMATURE | Yellow green 146B | Light brown 177D | Green 148A | Green 146D |
| FLOWER NECTARY COLOR, MATURE | Red purple 59A | Dark purple 187A | Green 146B/146C | Green 147A |
| STAMINOIDAL OUTLINE | Narrow, triangular | Broad, triangular | Medium, triangular | Narrow, triangular |
| STAMINOIDAL COLLAR COLOR, MATURE | Pale pink/purple | Pale pink/purple | White | Very pale pink/purple |

CHART A-continued

| CHARACTERISTIC | BLONDIE | PURPLE PRIDE, pollen parent | *Chamelaucium megapetalum* selection, seed parent | REVELATION |
|---|---|---|---|---|
| CALYX LOBE COLOR, MATURE | White | Pale pink/ purple | White | Pale purple |
| STYLE COLOR, MATURE | White | Purple | White | Light violet 84B |
| FLORAL TUBE FLUTING, IMMATURE | Prominent | Slight | Slight | Prominent |
| FLORAL TUBE OUTLINE | Flared | Flared | Conical | Flared |
| FLORAL TUBE DIAMETER | 4.3 mm | 7 mm | 6.8 mm | 6.8 mm |
| FLORAL TUBE COLOR, MIDPOINT | Green | Red/ brown | Green | Green |
| FLORAL TUBE COLOR, DISTAL END | Green | Red/ brown | Green | Purple brown |
| FLOWERING STEM SHAPE | Broad | Broad | Narrow | Broad |

It is claimed:

1. A new and distinct Chamelaucium interspecific hybrid plant named Blondie, as illustrated and described.

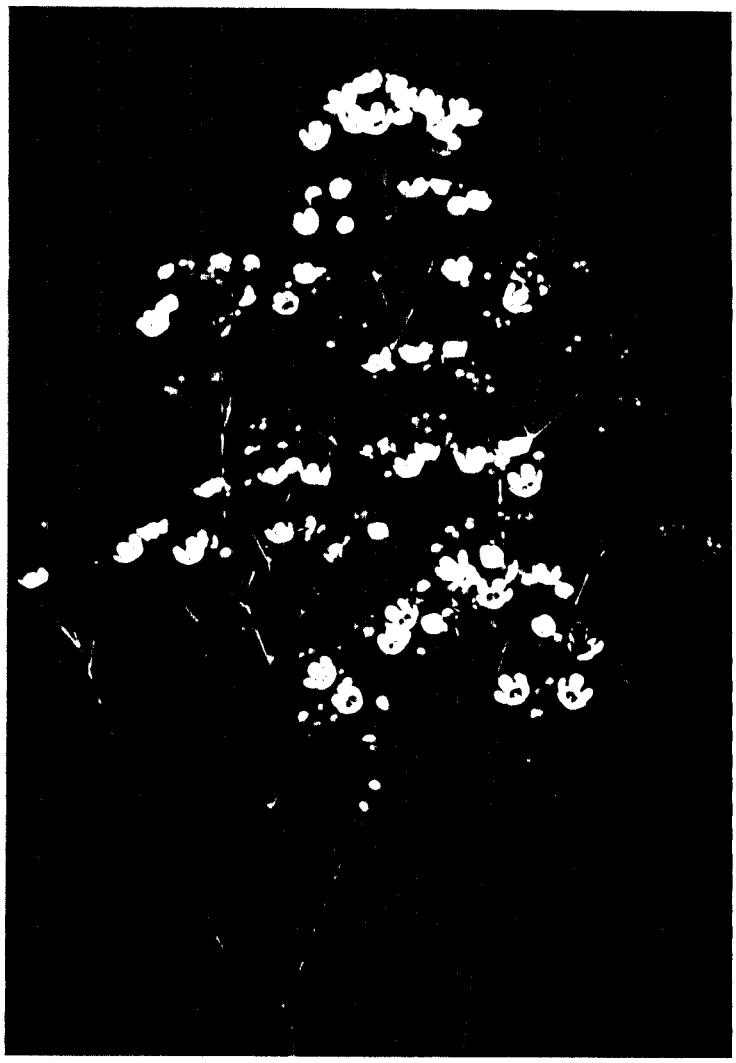

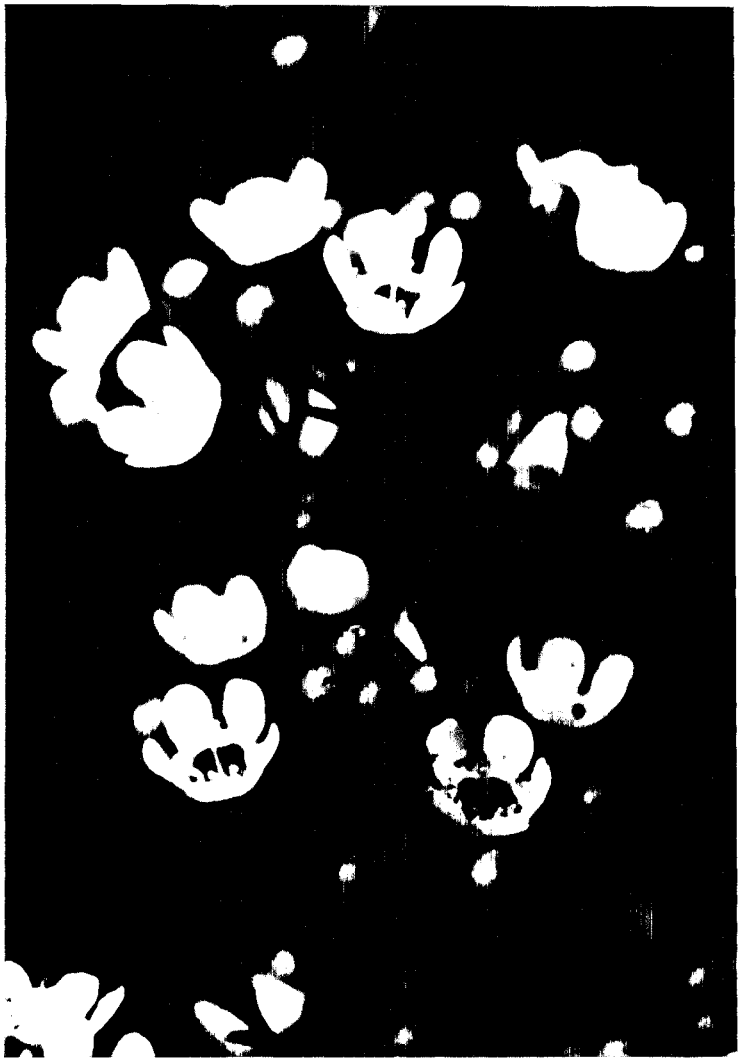

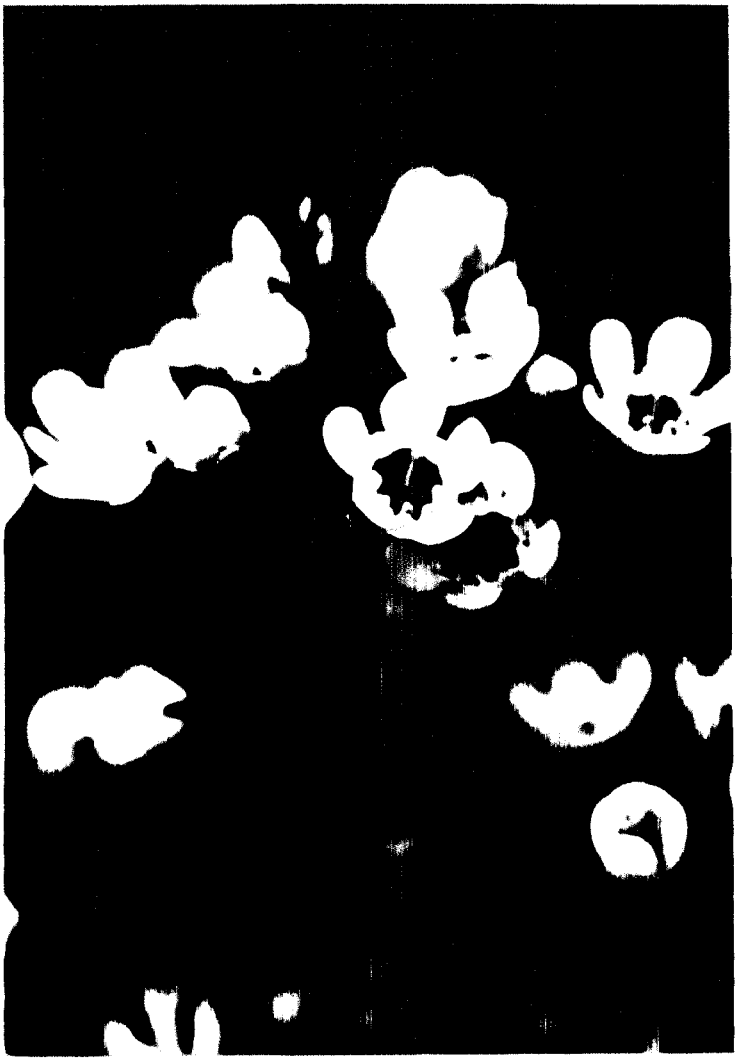

* * * * *